United States Patent [19]

Carrier

[11] Patent Number: Plant 5,294

[45] Date of Patent: Oct. 16, 1984

[54] CARNATION PLANT

[76] Inventor: Leonard E. Carrier, 1911 Sheridan Rd., Encinitas, Calif. 92024

[21] Appl. No.: 425,115

[22] Filed: Sep. 27, 1982

[51] Int. Cl.[3] ..... A01H 5/00

[52] U.S. Cl. ..... Plt./70

[58] Field of Search ..... Plt./70–71

*Primary Examiner*—Robert E. Bagwill

*Attorney, Agent, or Firm*—Frank B. Robb

[57] ABSTRACT

A new and distinct cultivar of carnation plant, with superior resistance to soil borne diseases, having small, finely, serrated flowers and a distinctive magenta flower color, which was originated by me by crossing numbered but unnamed and unpatented seedlings.

1 Drawing Figure

BACKGROUND AND DESCRIPTION OF THE INVENTION

The present invention relates to a new and distinct cultivar of Carnation plant which I designate as Lady Di and the numeral 1974 and which was originated by me in my commercial nursery at Encinitas, Calif. by cross-breeding numbered but unnamed and unpatented seedlings.

The primary objectives of this breeding have been to produce a carnation cultivar having improved disease resistance and production qualities, along with distinctive flower color, size and form, as well as less tendency of the calyx to burst and cause "splits" as the flowers open fully, which is so typical of the species botanically known as *Dianthus caryophyllus*. These objectives have been fully achieved, together with other desirable improvements, as evidenced by the following unique combination of principal characteristics which are outstanding in my new cultivar, Lady Di and which distinguish it from its parents, as well as from all other carnations of which I am aware:

1. A very vigorous and free-breaking plant habit with strong and straight stems;
2. Superior resistance to soil-borne diseases such as *Fusarium oxysporum* and *F. roseum,* and rots such as damping off, water molds, and the like;
3. Small, finely serrated flowers which open fully without bursting the calyx and causing "splits";
4. A distinctive and attractive magenta flower color which does not fade rapidly, but when fading takes place it occurs evenly and beautifully.

Asexual reproduction of my new carnation variety by side shoot cuttings rooted in peat and "Perlite" under mist, as performed under my direction and control at Encinitas, Calif., shows that the foregoing characteristics and distinctions come true and are established and transmitted through succeeding propagations.

The accompanying drawing illustrates typical specimens of the vegetative growth and flowers of my new carnation in different stages of development and is depicted in color as nearly true as it is reasonably possible to make the same in a color illustration of this character.

There follows a detailed description of my new carnation cultivar, Lady Di with color terminology in accordance with Robert Ridgeway's Color Standards and Nomenclature (1912 edition), except where general color terms of ordinary dictionary significance are suitably definitive.

PLANT

Botanical classification: *Dianthus caryophyllus.*

Breeding:

*Female parent.*—My designation — #929 an unnamed seedling (unpatented).

*Male parent.*—My designation — #1674 an unnamed seedling (unpatented).

Form: Erect but free-branching, angle of side bud to stem 25°.

Growth: Rapid, strong growth.

Classification: Greenhouse type, suitable for cut flower production as spray carnation (terminal removed and flowering side buds)

Propagation: Holds its distinguishing characteristics through succeeding propagations by rooted cuttings.

Locality where grown and observed: Encinitas, Calif.

Disease resistance: The new cultivar has shown no evidence of Fusarium or other rots, as determined by extensive tests in highly infested soils inoculated with as many strains of fungi as are locally available in the area of Encinitas, Calif.; tests were conducted without chemical or steam sterilization of the soil and in soils in which the carnation plant "Sim" and others soon die.

Temperature tolerance: Not hardy to cold, but grows best at temperature above 10° C.; has good resistance to hot weather in summer months of August and September at Encinitas, Calif., without hardening of growth and with only little reduction of flower size and little flower fading; no marked fading of outer flower petals even when bloom is past maturity.

Blooming period: Blooms under both long and short photoperiods.

Height: First crop 45 cm., later crops 50–55 cm.

BUD

Lobes of calyx overlap in tight bud and seldon split.

Length: 2.5 cm.

Diameter: 1.4 cm.

Color: Aster purple, plate x11, 67 v-r-L.

PEDUNCLE

Strength: Strong.

Color: Dark yellowish green; plate XVIII, 33'GY-G-M.

BLOOM

Size: Diameter 5 cm., depth 2 cm.

Stem: Consists of 9 nodes. Length is from about 50 cm. Diameter is from about 0.75 cm. at base and about 0.2 cm. at base of calyx.

*Color.*—Dark yellowish green, plate XVIII, 33'GY-G-M.

Form: Open, flat, crowned.

Petalage: From 35–50 petals. Outer petals are about 2.3 cm. wide and about 3 cm. long. Center petals are about 1 cm. wide and about 3 cm. long.

*Color.*—The center of flower, outer petals, base of petals, inside of petals and reverse of petals are all aster purple, plate XII, 67 V-R-i.

*General tonality.*—Uniform aster purple with few marginal white lines.

Petals:

Texture is soft.

*Form.*—Roughly 30°, circle, irregular serrations 10 per cm.

*Opening.*—Normal with minimum of split calyxes.

*Fragrance.*—No distinctive fragrance.

FOLIAGE

Form: Flat to concave.

Size: 0.8 cm. wide and 16 cm. long.

Quantity: Two leaves per node, with nodes spaced about 8 cm. apart.

Color: The upper and under sides of young plants — winter green, plate XVIII, 33'GY-G-i. Mature plants, plate XVIII, 33'GY-G-M.

Texture: Smooth.

I claim:

1. A new and distinct cultivar of carnation plant designated Lady Di substantially as herein shown and decribed, characterized particularly as to novelty by the unique combination of a very vigorous and free-breaking plant habit, and strong and straight stems, superior resistance to soil-borne diseases, including *Fusarium oxysporum* and *F. roseum* and rots such as damping off, water molds, small, finely, serrated flowers which open fully without bursting the calyx and causing "splits", a distinctive and attractive magenta flower color which fades evenly and beautifully, and good heat tolerance which is superior to that of the parent lines and the variety known as "Sim".

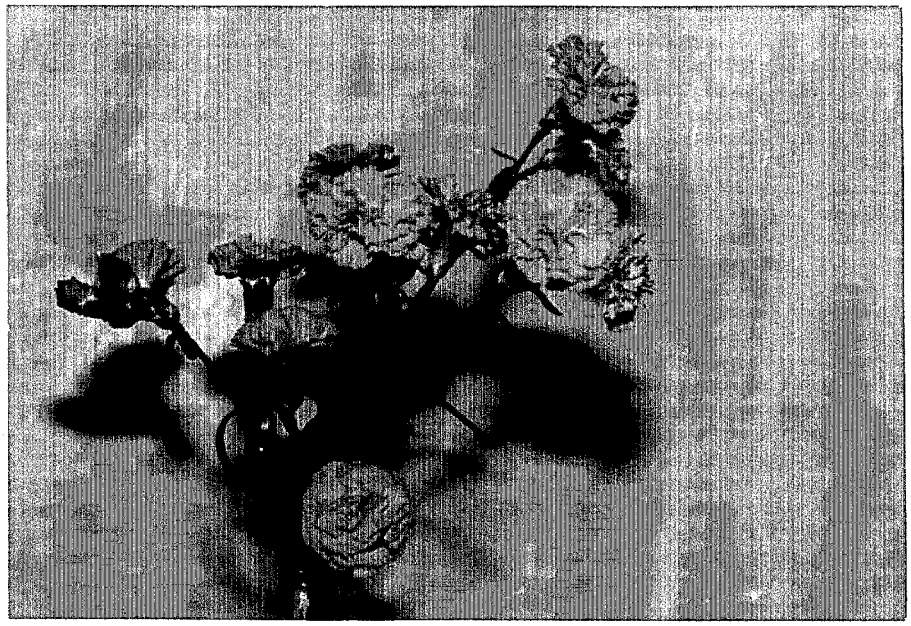

* * * * *